United States Patent
Walsh et al.

(10) Patent No.: US 6,547,765 B1
(45) Date of Patent: Apr. 15, 2003

(54) DEVICE FOR INTUBATING LACRIMAL DUCTS

(75) Inventors: David J. Walsh, Waterdown (CA); William Whittington, Oakville (CA)

(73) Assignee: Walsh Medical Devices Inc., Oakville (CA)

(*) Notice: Subject to any disclaimer, the term of this patent is extended or adjusted under 35 U.S.C. 154(b) by 0 days.

(21) Appl. No.: 09/161,776

(22) Filed: Sep. 29, 1998

(51) Int. Cl.$^7$ .......................... A61M 25/00; A61M 5/00
(52) U.S. Cl. ..................... 604/264; 604/8; 604/523
(58) Field of Search .................. 604/8, 264, 523, 604/9, 10, 164, 500, 506, 513, 514, 516, 165.01–165.02, 271, 274, 533–535, 539, 294, 174, 175; 403/28, 273, 223; 138/120, 118, 155; 128/348, 772; 606/107, 108, 110, 113; 600/585; 285/381.4

(56) References Cited

U.S. PATENT DOCUMENTS

| | | | |
|---|---|---|---|
| 2,154,968 A | 4/1939 | Alkio | 128/348 |
| 3,948,272 A | 4/1976 | Guibor | 128/350 R |
| 4,305,395 A | * 12/1981 | Martinez | 128/348 |
| 4,380,239 A | 4/1983 | Crawford et al. | 694/28 |
| 5,437,625 A | 8/1995 | Kurihashi | 604/8 |
| 6,117,116 A | * 9/2000 | Walsh | 604/264 |

FOREIGN PATENT DOCUMENTS

FR    2700722 A1    1/1993

* cited by examiner

Primary Examiner—Angela D. Sykes
Assistant Examiner—Patricia M. Bianco
(74) Attorney, Agent, or Firm—Ingrid E. Schmidt

(57) ABSTRACT

In accordance with the invention, an intubation set is provided having an improved connector between the tube and a probe. In a preferred embodiment, the connector includes a deformable sleeve which at one end receives an end of the tube and at the other end is tapered to converge on the probe where it is permanently attached. The tube contains a solid insert which can be set in a compound such as silicone rubber and the sleeve is deformed radially inwardly to trap part of the tube containing the insert thereby locking the tube to the sleeve and hence to the probe. A method of making the intubation set is also provided. The invention also provides an improved intubation set for use in intubating the canaliculi without probing a healthy nasolacrimal duct.

22 Claims, 2 Drawing Sheets

DEVICE FOR INTUBATING LACRIMAL DUCTS

FIELD OF THE INVENTION

The present invention relates to devices for intubating lacrimal ducts and more particularly to intubation sets for positioning a length of tubing in the lacrimal ducts.

BACKGROUND OF THE INVENTION

The insertion of an elongate length of tubing member in the lacrimal ducts is a common surgical procedure for reconstruction or other remedial purposes. Lacrimal fluid or tears are continuously supplied from the lacrimal gland to wash across the sclera and other conjunctival components and the cornea. The excess lacrimal fluid is drained through a network of passages commencing with the puncta which appear as small papilla adjacent the inner canthus or inner corner of the eye, the lacrimal fluid being collected in the lacrimal sac by a number of canaliculi connecting the puncta with the lacrimal sac. The lacrimal sac is drained through the nasolacrimal duct which passes into the inferior nasal meatus. This network of passages is referred to hereinafter as the lacrimal ducts.

Closures of the lacrimal ducts can occur as a result of congenital anomalies, accidents, inflammation, advanced aging, as well as other physiological conditions. The closures prevent drainage of tears so that the affected eyes are continually brimming over with fluid, causing much personal discomfort to the patient, and often causing infection and/or inflammation of the mucous membranes as well as other undesirable conditions.

Known devices for correcting blocked lacrimal ducts include an intubation set disclosed in U.S. Pat. No. 4,380,239 to Dr. John Crawford, et al. The intubation set includes a probe consisting of a light resilient wire which can be readily deflected through an angle of at least 90 degrees to permit the probe to pass from the nasolacrimal duct to the inferior nasal meatus. The probe has a tip or distal end which is slightly enlarged and rounded to limit the possibility of damage to tissue when the probe is inserted, and a proximal end provided with an enlargement. A very flexible tube of minimal rigidity has a first end which is in engagement over the wire at the proximal end and into contact with the enlargement. Adhesive can be used to improve the connection.

When in use, the probe is inserted through either an upper punctum or a lower punctum of the lacrimal ducts and is guided downwardly through the lacrimal ducts to the inferior nasal meatus whereupon a tool in the form of a hook (shown in the Crawford patent) is used to pull the probe through the nostril leaving a length of tubing extending through the full length of the lacrimal ducts.

Although the Crawford intubation set provides a relatively secure connection between the tube and the probe, in rare instances these components have been found to separate during the intubation procedure. The cause is believed to be contact with bony structure which tends to roll the tube off the wire. Although this event is unusual, it would be preferable to provide an intubation device which benefits from the principles taught in the Crawford patent and which also has a connection between the probe and the tube which is less likely to suffer from this problem.

It is also possible for a closure to occur in the canaliculi and not in the nasolacrimal duct. For instance, the canaliculi may suffer traumatic injury while the nasolacrimal duct remains unaffected. It is therefore also desirable to provide an intubation set adapted to position a length of tubing in the region of the canaliculi without probing the healthy nasolacrimal duct in order to facilitate intubation by a physician.

SUMMARY OF THE INVENTION

In accordance with an aspect of the invention, an intubation set is provided having an improved connector between a tube and a probe. In a preferred embodiment, the connector includes a deformable sleeve which at one end receives an end of the tube and at the other end is tapered to converge on the probe where it it is permanently attached. The tube contains a solid insert which can be set in a compound such as silicone rubber and the sleeve is deformed radially inwardly to trap part of the tube containing the insert thereby locking the tube to the sleeve and hence to the probe. A method of making the intubation set is also provided.

The invention also provides an improved intubation set for use in intubating the canaliculi without probing a healthy nasolacuimal duct. In this case the probe is bent into a predefined spiral configuration and preferably lies in a plane. A tip on the probe can be pulled out of the plane to create a spiral for easier insertion. The spiral can be clockwise or anticlockwise depending on which way the tip is pulled out of the plane.

These and other aspects of the invention will be better understood with reference to the following description and drawings.

BRIEF DESCRIPTION OF THE DRAWINGS

Preferred embodiments of the invention will now be described with reference to the drawing in which.

DETAILED DESCRIPTION OF THE PREFERRED EMBODIMENTS

Figure 1:
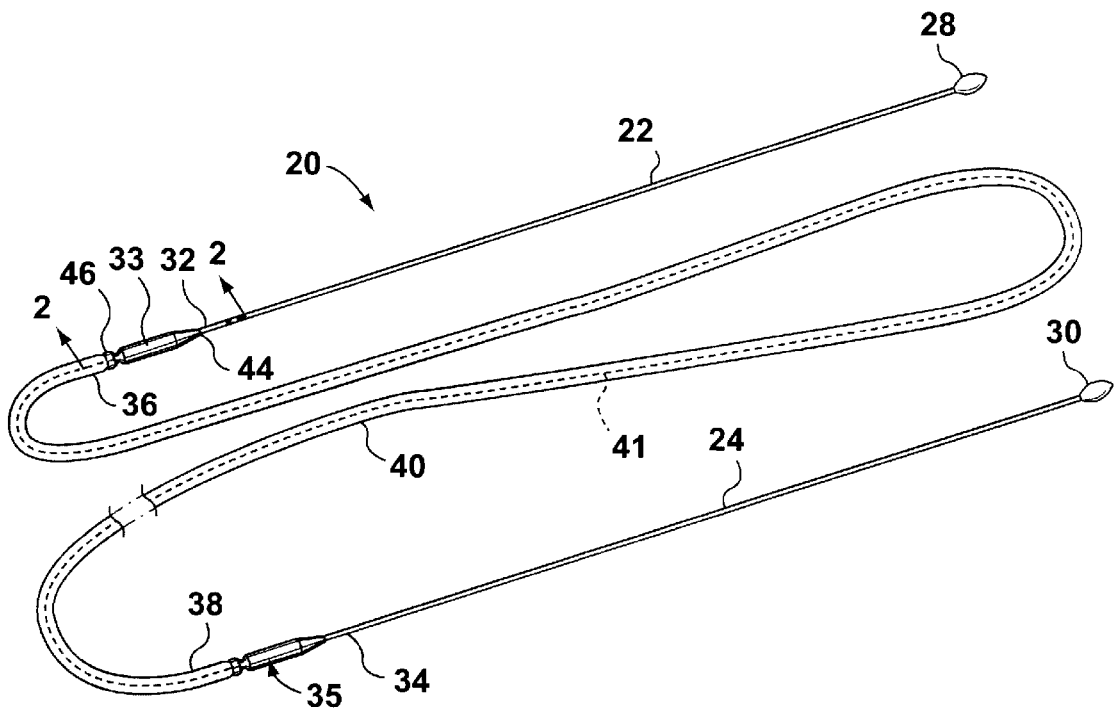
FIG. 1 is a diagrammatic view of an intubation set according to a first preferred embodiment of the invention.

Reference is first made to FIG. 1 which illustrates an intubation set designated generally by the numeral 20 according to a first preferred embodiment of the invention. The intubation set 20 can be used according to a procedure described in the aforementioned U.S. Pat. No. 4,380,239 to Dr. Crawford. The procedure has become well established and uses a tool described in the Crawford patent. The same tool can be used with the present intubation set 20 to pull the probe from the nasal passage.

The intubation set 20 preferably includes a pair of similar thin probes 22, 24 of a light stainless steel wire which can be resiliently deflected to pass from the nasolacrimal duct to the inferior nasal meatus. The probes 22, 24 have enlarged and olive-shaped tips 28, 30, respectively, to limit the possibility of damage to tissue when one of the probes 22, 24 is inserted, and proximal end portions 32, 34 respectively.

It has been found that an olive-shaped tip meets with less resistance than a more rounded tip, as taught by the Crawford patent and results in easier insertion of the probe through the lacrimal ducts.

The end portions 32, 34 of probes 22, 24, respectively, are securely coupled by connectors 33, 35 to respective first and second end portions 36, 38 of a very flexible resiliently deformable, medical grade silicone rubber tube 40 of minimal rigidity, as will be described.

A length of silk 6/O suture 41 extends through the tube 40 along its full length and is used to tie cut ends of the tube 40 together after the tube 40 has been positioned in the lacrimal ducts, as is common in the art.

Figure 2:
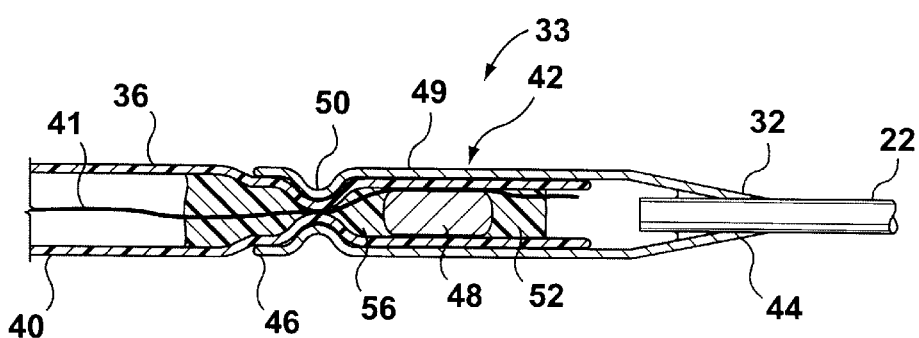
FIG. 2 is a side sectional view taken generally on line 2—2 of FIG. 1 and drawn to a larger scale to illustrate a connector used to attach a tube to a probe of the intubation set.

FIG. 2 illustrates the connector 33 in more detail. This connector is also typical of connector 35 and connects the end portion 36 of the tube 40 to the proximal end portion 32 of the probe 22.

A thin-walled stainless steel tubular sleeve designated generally by reference numeral 42, has a tapered leading end 44, a trailing end 46 and a crimped intermediate portion 50. The leading end 44 is silver soldered to the end portion 32 of the probe 22 with a portion of the proximal end portion 32 of the probe 22 extending within the sleeve 42.

The end portion 36 of the tube 40 extends inside the sleeve 42 and is secured by the combination of a cylindrical insert 48 of solid stainless steel, and the crimped portion 50 of the trailing end 46 of the sleeve 42 as will be described.

The insert 48 is assembled in the connector by first entering a first quantity of uncured silicone sealer 56 into the tube, followed by the insert 48 and finally by a second quantity of uncured sealer 52.

After curing, the tube, together with a sealer and the insert 48, is entered into the sleeve 42 and deformed by crimping to form the portion 50 which locks the tube in place. The cured silicone will combine with the insert 48 to create a structure which can not be withdrawn through the radially decreased crimped intermediate portion 50. The resistance to separation is enhanced by the rigid insert 48 because the insert is larger than the internal diameter of the crimped intermediate portion 50. Also, because the silicone locks the insert in the tube, the insert cannot escape from the tube to allow the tube to be removed without the insert.

The connector 33 provides a smooth tapered transition from the probe 22 to to a generally cylindrical portion 49 of the sleeve 42. Consequently, as the intubation set 20 is advanced in the lacrimal ducts, the smooth transition will ensure there will be little likelihood of snags thereby minimizing the discomfort to the patient.

The dimensions and other characteristics of the intubation set 20 will now be discussed followed by a discussion of alternative structures.

The probes 22, 24 are of tempered stainless steel wire having a diameter of approximately 0.4 mm and exhibit a resistance to deflection to retain their original shape after being subjected to small deflections as they are moved through the lacrimal ducts. Such fine wires would, of course, puncture tissue if the ends of the wires did not include the enlarged tips 28, 30.

The length of the probes 22, 24 is approximately 110 mm. The silicone rubber tube 40 has an outer diameter of about 0.6 mm, an inner diameter of about 0.3 mm and a length of about 300 mm. The sleeve 42 is deformable stainless steel having a length of about 11 mm. The generally cylindrical portion 49 of the sleeve 42 has an outer diameter of about 0.8 mm and an inner diameter of about 0.6 mm.

One of the advantages of the present invention is that there is provided a very secure means of connecting the tube 40 to the probes 22, 24 such that the risk of separation of the tube 40 from any one of the probes 22, 24 is minimized.

Many variations to the intubation set 20 thus described and the method of its manufacture are possible within the scope of the invention. For example, the length of the probe may range from about 50 mm to about 150 mm.

As well, the length of the sleeve may be from about 6 mm to about 16 mm. Further, the outer diameter of the generally cylindrical portion of the sleeve may be from about 0.7 mm to about 1.0 mm.

Additionally, the deformation of the sleeve resulting in portion 50 may be by any suitable method, including rolling or swaging.

The intubation set may consist of a single probe coupled to a tube rather than a pair of probes coupled to respective ends of a tube.

Further, the tube need not contain a length of silk suture extending therethrough.

Figure 3:
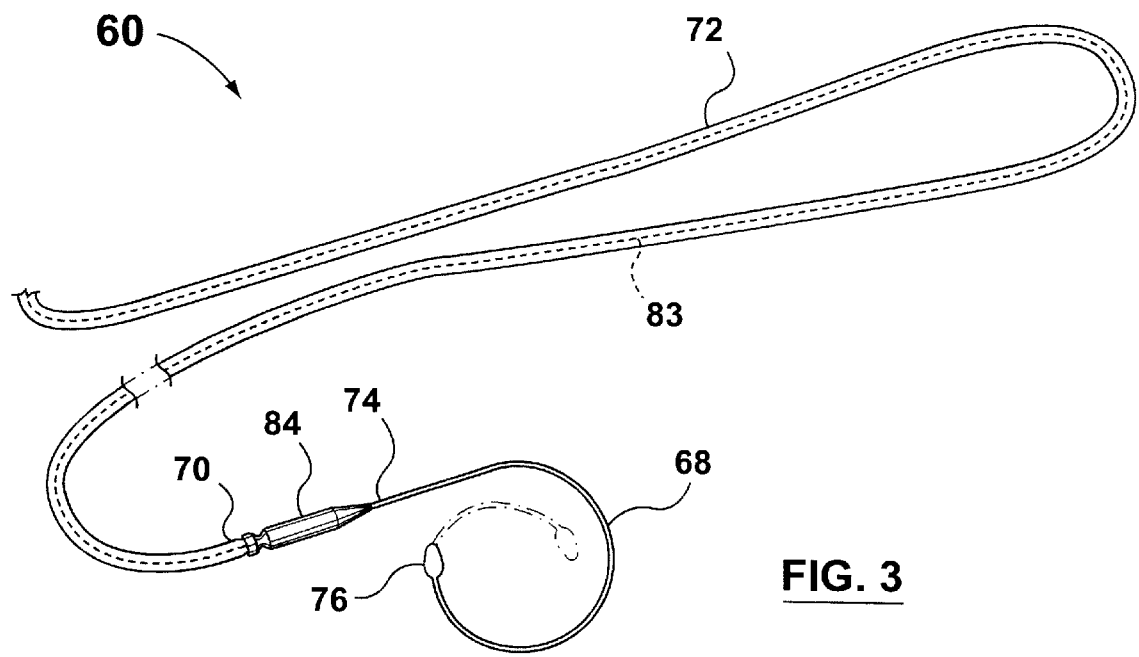
FIG. 3 is a diagrammatic view of part of an intubation set according to a second preferred embodiment of the invention.
Figure 4:
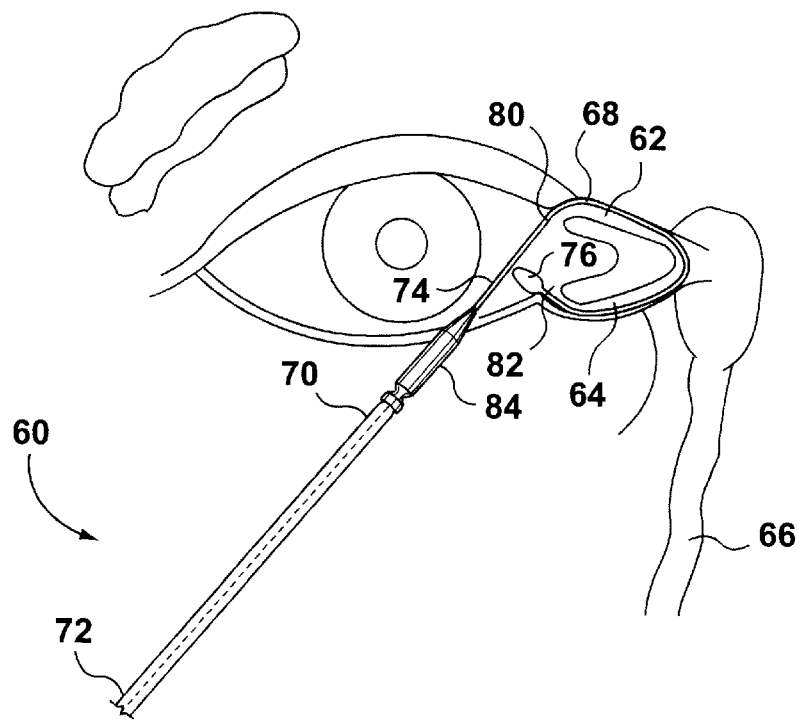
FIG. 4 is a diagrammatic view showing the intubation set of FIG. 3 in use to intubating the canaliculi of a patient.

Reference will now be made to FIGS. 3 and 4 which illustrate an intubation set designated generally by reference numeral 60 according to a second preferred embodiment of the invention. The intubation set 60 is specially adapted for intubating only the upper and lower canaliculi 62, 64 respectively, without probing the nasolacrimal duct 66 (FIG. 4). Thus, the intubation set 60 is to be preferred to the intubation set 20 when a blockage occurs only in the canaliculi of the patient. In such case, it would be simpler and easier to probe the canaliculi using the intubation set 60 than to probe the canaliculi and nasolacrimal duct using the intubation set 20.

The intubation set 60 is similar in every respect to the intubation set 20 except for the dimensions of the component parts, and the configuration and material of the probes. Specifically, the intubation set 60 includes a pair of similar spiral probes 68, (one of which is shown) bent into a predefined spiral shape. The probe is a resilient, stiff, stainless steel wire having a proximal end portion 74 secured to a portion 70 of a very flexible resiliently deformable silicone rubber tube 72 of minimal rigidity containing a length of 6/0 silk suture 83 extending through the full length of the tube 72.

The intubation set may be used in two ways. One ways illustrated in FIG. 4, is to insert the probe through an upper punctum 80, feed the probe into the upper canaliculus 62, move the probe downwardly into and through the lower canaliculus 64, and finally move the probe out through the lower punctum 82. The probe 68 is then pulled away from the patient by the tip 76 until a portion of the tube 72 is positioned through the canaliculi. Afterwards, the tube 72 is cut in two locations adjacent respective upper and lower puncta 80, 82. Portions of the tube 72 near the cut ends thereof are peeled away revealing ends of the silk suture 83 which are then tied together, thereby forming the portion of the tube 72 retained in the canaliculi into a loop, in accordance with established practice.

Another method of using the intubation set 60, which is not illustrated, involves inserting one of the spiral probes through one of the upper and lower puncta, inserting the other of the spiral probes through the other of the upper and lower puncta, and feeding the probes through respective canalicula until they meet at a location where the canaliculus is severed due to trauma to the region. The probes are then removed through an incision or open wound in the patient at the severed location, thereby leaving a length of tubing in the canaliculi. The tube is then cut in two locations adjacent the incision or wound, to form cut ends of the tube and suture. The cut ends of the tube are peeled away to reveal cut ends of the silk suture, and the cut ends of the silk suture are then tied together to form the tube into a loop.

The intubation set 60 further includes connectors 84 (one of which is seen) coupling the probe 68 to the tube 72 in the same manner as described with reference to the intubation set 20.

The wire of the probe has a diameter of about 0.6 mm and a length of about 50 mm.

As in the case of the intubation set 20 according to the first preferred embodiment, variations to the second preferred embodiment are possible without departing from the scope of the invention.

For example, the probe set shown in FIGS. 3 and 4 has a different use from the probe set 20 and may be made using known connections between the tube and the probes while still providing a novel structure. The spiral probe may be secured to the silicone tube in any number of ways such as by using an adhesive or the joint taught in U.S. Pat. No. 4,380,239 to Crawford et al.

The spiral probe may be made of annealed stainless steel which is more easily deformable and less resilient.

The wire of the probe may have a diameter of from about 0.4 mm to about 0.8 mm, and a length of from about 37 mm to about 75 mm.

The intubation set may consist of a single spiral probe secured to a tube rather than a pair of spiral probes secured to respective end portions of a tube.

It should be understood that the foregoing description of the preferred embodiments are by way of example only and should not be construed as limiting the scope of the invention as defined by the following claims.

What is claimed is:

1. An intubation set for use in the canaliculus intubation of the lacrimal ducts, the intubation set including
    a probe of a light wire which can be resiliently deflected to pass from the nasolacrimal duct to the inferior nasal meatus, the probe having an enlarged and olive-shaped tip to limit the possibility of damage to tissue when the probe is inserted, and a proximal end portion;
    a tubular sleeve having a leading end, a trailing end, and a generally cylindrical portion intermediate said leading end and said trailing end, said leading end being attached to said proximal end portion of the probe;
    a very flexible resiliently deformable tube of minimal rigidity having first and second end portions and containing a solid insert securely fixed within said first end portion; and
    wherein the insert is disposed within said generally cylindrical portion of the sleeve and a diameter of a portion of the sleeve intermediate said generally cylindrical portion and said trailing end is reduced to trap the insert inside the sleeve thereby securing the tube to the sleeve and hence to the probe.

2. A probe set according to claim 1 wherein said second end portion contains a second solid insert securely fixed within said second end portion, the probe set further including
    a second probe of a light wire which can be resiliently deflected to pass from the nasolacrimal duct to the inferior nasal meatus, the second probe having an enlarged and olive-shaped second tip to limit the possibility of damage to tissue when the second probe is inserted, and a second probe proximal end portion;
    a second generally tubular sleeve having a second sleeve leading end, a second sleeve trailing end, and a second sleeve generally cylindrical portion intermediate said second sleeve leading end and said second sleeve trailing end, said second sleeve leading end being attached to said second probe proximal end portion;
    wherein the second insert is disposed within said second sleeve generally cylindrical portion and a diameter of a portion of the second sleeve intermediate said second sleeve generally cylindrical portion and said second sleeve trailing end is reduced to trap the second insert inside the second sleeve thereby securing the tube to the second sleeve and hence to the probe.

3. An intubation set according to claim 1 wherein said solid insert is of stainless steel and is secured within cured silicone within said first end portion.

4. An intubation set according to claim 1 adapted to intubate the canaliculi of the lacrimal ducts wherein at least the tip of the said probe is bent into a predefined spiral shape.

5. An intubation set according to claim 1 wherein said sleeve is tapered from said generally cylindrical portion of the sleeve toward said proximal end portion of the probe to provide a smooth transition from the probe to the sleeve.

6. An intubation set according to claim 1 wherein said wire of said probe is of stainless steel and has a diameter of about 0.4 mm and a length of from about 50 mm to about 150 mm.

7. An intubation set according to claim 1 wherein said tube is of silicone rubber and has an outer diameter of about 0.6 mm, an inner diameter of about 0.3 mm and a length of about 300 mm.

8. An intubation set according to claim 1 wherein the tube contains a length of silk suture extending through the tube along the full length of the tube.

9. An intubation set for use in intubating only the canaliculi of the lacrimal ducts, wherein the intubation set includes
    a spiral probe of a light wire having a tip bent into a predefined spiral shape which can be deflected to pass through the puncta and through the canaliculi, the probe having a tip and a proximal end portion; and
    a very flexible resiliently deformable tube of minimal rigidity having a first leading end portion and a second trailing end portion, said leading end portion being secured to the proximal end portion of the probe, and the second trailing end portion being remote from said proximal end portion of the probe.

10. An intubation set according to claim 9 further including a second spiral probe of a light wire having a tip bent into a predefined spiral shape which can be deflected to pass through the puncta and through the canaliculi, the probe having a second probe tip and a second probe proximal end portion, wherein said second trailing end portion of the tube is secured to said second probe proximal end portion.

11. An intubation set according to claim 9 further including a tubular sleeve having a leading end, a trailing end, a generally cylindrical portion intermediate said leading end and said trailing end, and wherein
    said leading end is attached to said proximal end portion of said probe;
    said tube contains a solid insert securely fixed within said first end portion;
    said insert is disposed within said generally cylindrical portion of the sleeve; and
    a diameter of a portion of the sleeve intermediate said generally cylindrical portion and said trailing end is reduced to trap the insert inside the sleeve thereby securing the tube to the sleeve and hence to the probe.

12. An intubation set according to claim 9 wherein the tube contains a length of silk suture extending through the tube along the full length of the tube.

13. An intubation set according to claim 9 wherein said wire of said probe is of stainless steel and has a diameter of from about 0.4 mm to about 0.8 mm and a length of from about 37 mm to about 75 mm.

14. An intubation set according to claim 9 wherein the tip of the probe is enlarged and olive-shaped to limit the possibility of damage to tissue when the probe is inserted.

15. An intubation set comprising
  a stainless steel probe having an enlarged, olive-shaped tip at one end and a proximal end;
  a very flexible tube of minimal rigidity to be placed in the intubation set;
  a connector including a deformable sleeve having a tapered leading end converging on the probe and attached to the proximal end of the probe, and a trailing end, a solid insert engaged in an end portion of the flexible tube with the end portion of the tube containing the insert being contained in the sleeve, and the sleeve being deformable adjacent the trailing end to trap said portion of the tube and the insert in the sleeve to thereby connect the tube to the probe.

16. An intubation set as claimed in claim 15 in which at least the tip of the probe is bent into a predefined spiral shape.

17. An intubation set as claimed in claim 16 in which the probe lies in a plane so that by displacing the tip from the plane, a generally helical spiral can be created having either a clockwise or anticlockwise spiral as required.

18. An intubation set as claimed in claim 15 in which the connector further includes silicone embedding the insert in the tube.

19. An intubation set for use in the canaliculus intubation of the lacrimal ducts, the intubation set including
  a probe of a light wire which can be resiliently deflected to pass from the nasolacrimal duct to the interior nasal meatus, the probe having an enlarged and olive-shaped tip to limit the possibility of damage to tissue when the probe is inserted, and a proximal end portion;
  a tubular sleeve of a stainless steel having a leading end, a trailing end, and a generally cylindrical portion intermediate said leading end and said trailing end, an outer diameter of from about 0.7 mm to about 1.0 mm and an inner diameter of about 0.6 mm, and a length of from about 6 mm to about 16 mm, said leading end being attached to said proximal end portion of the probe;
  a very flexible resiliently deformable tube of minimal rigidity having first and second end portions and containing a solid insert securely fixed within said first and end portion; and
  wherein the insert is disposed within said generally cylindrical portion of the sleeve and a diameter of a portion of the sleeve intermediate said generally cylindrical portion and said trailing end is reduced to trap the insert inside the sleeve thereby securing the tube to the sleeve and hence to the probe.

20. A probe set according to claim 19 wherein said second end portion contains a second solid insert securely fixed within said second end portion, the probe set further including
  a second probe of light wire which can be resiliently deflected to pass from the nasolacrimal duct to the inferior nasal meatus, the second probe having an enlarged and olive-shaped second tip to limit the possibility of damage to tissue when the second probe is inserted, and a second probe proximal end portion;
  a second generally tubular sleeve of stainless steel having a second sleeve leading end, a second sleeve trailing end, and a second sleeve generally cylindrical portion intermediate said second sleeve leading end and said second sleeve trailing end having an outer diameter of from about 0.7 mm to about 1.0 mm and an inner diameter of about 0.6 mm, and a length of from about 6 mm to about 16 mm, said second sleeve leading end being attached to said second probe proximal end portion;
  wherein the second insert is disposed within said second sleeve generally cylindrical portion and a diameter of a portion of the second sleeve intermediate said second sleeve generally cylindrical portion and said second sleeve trailing end is reduced to trap the second insert inside the second sleeve thereby securing the tube to the second sleeve and hence to the probe.

21. An intubation set including a spiral probe having a tip bent into a predefined spiral shape which can be deflected to pass through the puncta and through the canaliculi, the probe having a tip and a proximal end portion;
  a very flexible resiliently deformable tube of minimal rigidity having a first leading end portion and a second trailing end portion, said first leading end portion being secured to the proximal end portion of the probe, and the second trailing end portion being remote from said proximal end portion of the probe;
  a tubular sleeve of stainless steel having a leading end, a trailing end, a generally cylindrical portion intermediate said leading end and said trailing end, and wherein said leading end is coupled to said proximal end portion of said probe;
  said tube contains a solid insert securely fixed within said first end portion;
  said insert is disposed withing said generally cylindrical portion of the sleeve; and
  a diameter of a portion of the sleeve intermediate said generally cylindrical portion and said trailing end is reduced to trap the insert inside the sleeve thereby securing the tube to the sleeve and hence to the probe.

22. An intubation set comprising
  a stainless steel probe having a tip at one end and a proximal end;
  a very flexible tube of minimal rigidity to be placed in the intubation set; and
  a connector including a deformable stainless steel sleeve having a tapered leading end converging on the probe and coupled to the proximal end of the probe, and a trailing end, a solid insert engaged in an end portion of the flexible tube with the end portion of the tube containing the insert being contained in the sleeve, the sleeve being deformable adjacent the trailing end to trap said portion of the tube and the insert in the sleeve to thereby connect the tube to the probe.

* * * * *